United States Patent
Kawada et al.

(10) Patent No.: US 9,612,153 B2
(45) Date of Patent: Apr. 4, 2017

(54) ELECTRIC FIELD VECTOR DETECTION METHOD AND ELECTRIC FIELD VECTOR DETECTION DEVICE

(71) Applicant: HAMAMATSU PHOTONICS K.K., Hamamatsu-shi, Shizuoka (JP)

(72) Inventors: Yoichi Kawada, Hamamatsu (JP); Takashi Yasuda, Hamamatsu (JP); Hironori Takahashi, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 0 days.

(21) Appl. No.: 14/950,617

(22) Filed: Nov. 24, 2015

(65) Prior Publication Data

US 2016/0146666 A1    May 26, 2016

(30) Foreign Application Priority Data

Nov. 26, 2014 (JP) ................... 2014-238686

(51) Int. Cl.
*G01J 5/02* (2006.01)
*G01J 1/44* (2006.01)
(Continued)

(52) U.S. Cl.
CPC ............. *G01J 1/44* (2013.01); *G01J 1/0429* (2013.01); *G01J 1/4228* (2013.01);
(Continued)

(58) Field of Classification Search
CPC .......... G01J 1/0429; G01J 1/4228; G01J 1/44; G01J 3/4338; G01J 4/04; G01R 15/241; G01R 29/0871
(Continued)

(56) References Cited

U.S. PATENT DOCUMENTS 6,828,558 B1 * 12/2004 Arnone ............... G01N 21/49
    250/341.1
7,851,761 B2 * 12/2010 Popa-Simil ............ H01Q 19/30
    250/341.1

(Continued)

FOREIGN PATENT DOCUMENTS

GB        2347756        9/2000
WO    WO 2013/077097    5/2013

OTHER PUBLICATIONS

Author:Wenqi Zhu and Ajay Nahata, Title: Electric field vector characterization of terahertz surface plasmons, Date:2007, Publisher: Optical Society of America.*

(Continued)

*Primary Examiner* — David J Makiya
*Assistant Examiner* — Taeho Jo
(74) *Attorney, Agent, or Firm* — Drinker Biddle & Reath LLP

(57) ABSTRACT

In this electric field vector detection method, an electro-optic crystal, where a (111) surface of an optical isotropic medium is cut out, is used as a terahertz wave detection element. The method includes: causing polarization of probe light of ultrashort pulsed light to be circular polarization; allowing the probe light having circular polarization to enter the terahertz wave detection element and probing the terahertz wave; modulating the probe light, having probed the terahertz wave, by a rotating analyzer and detecting the modulated probe light by a photodetector; performing lock-in detection of a detection signal from the photodetector by a lock-in detector using a frequency based on a rotational frequency of the rotating analyzer as a reference signal; and detecting an electric field vector of the terahertz wave based on a detection signal from the lock-in detector.

10 Claims, 7 Drawing Sheets

(51) Int. Cl.
*G01J 4/04* (2006.01)
*G01J 1/42* (2006.01)
*G01J 1/04* (2006.01)
*G01J 3/433* (2006.01)
*G01J 3/42* (2006.01)
*G01J 3/02* (2006.01)
*G01R 15/24* (2006.01)
*G01R 29/08* (2006.01)
*G01N 21/3581* (2014.01)

(52) U.S. Cl.
CPC ........... *G01J 3/0224* (2013.01); *G01J 3/0262* (2013.01); *G01J 3/42* (2013.01); *G01J 3/433* (2013.01); *G01J 3/4338* (2013.01); *G01J 4/04* (2013.01); *G01J 2001/4242* (2013.01); *G01N 21/3581* (2013.01); *G01R 15/241* (2013.01); *G01R 29/0871* (2013.01)

(58) Field of Classification Search
USPC ....................................................... 250/341.3
See application file for complete search history.

(56) References Cited

U.S. PATENT DOCUMENTS

| | | | | |
|---|---|---|---|---|
| 2002/0153874 A1* | 10/2002 | Jiang | ................ | G01N 21/3581 324/96 |
| 2003/0165003 A1* | 9/2003 | Ciesla | ................ | G01N 21/3581 359/326 |
| 2005/0156607 A1* | 7/2005 | Okamura | .............. | G01F 23/284 324/639 |
| 2005/0230625 A1* | 10/2005 | Zhang | ................ | G01N 21/3581 250/341.1 |
| 2006/0132793 A1* | 6/2006 | Ogawa | ................ | G01M 11/331 356/484 |
| 2007/0273357 A1* | 11/2007 | Saito | ........................ | G01J 11/00 324/71.5 |
| 2007/0282206 A1* | 12/2007 | Arnone | ................ | A61B 5/0059 600/473 |
| 2010/0264904 A1* | 10/2010 | Wu | .................... | G01R 29/0885 324/97 |
| 2013/0284929 A1* | 10/2013 | Ouchi | .................. | G02F 1/3511 250/339.01 |
| 2014/0198973 A1* | 7/2014 | Zhang | ................ | G01N 21/3586 382/149 |
| 2014/0264032 A1* | 9/2014 | Neshat | ...................... | G01J 3/42 250/339.08 |
| 2015/0316832 A1* | 11/2015 | Sato | ........................ | G02F 1/365 250/338.1 |

OTHER PUBLICATIONS

M. B. Byrne et al., "Simultaneous measurement of orthogonal components of polarization in a free-space propagating terahertz signal using electro-optic detection," Applied Physics Letters, Apr. 12, 2011, pp. 151104-1-151104-3, vol. 98.

Nick C. J. van der Valk et al., "Terahertz polarization imaging," Optics Letters, Oct. 15, 2005, pp. 2802-2804, vol. 30, No. 20.

Naoya Yasumatsu et al., "Precise real-time polarization measurement of terahertz electromagnetic waves by a spinning electro-optic sensor," AIP Review of Scientific Instruments, Feb. 16, 2012, pp. 023104-1-023104-7, vol. 83.

Natsuki Nemoto et al., "Highly precise and accurate terahertz polarization measurements based on electro-optic sampling with polarization modulation of probe pulses," Optics Express, Jul. 16, 2014, pp. 17915-17929, vol. 22, No. 15.

Naoya Yasumatsu et al., "High-speed terahertz time-domain polarimeter based on an electro-optic modulation technique," Applied Physics Express, Sep. 4, 2014, pp. 092401-1-092401-4, vol. 7.

Su Sheng-Kai et al., "Low temperature and high magnetic field spectroscopic ellipsometry system", Review of Scientific Instruments, vol. 85, No. 5, published online May 1, 2014, pp. 1-9.

* cited by examiner

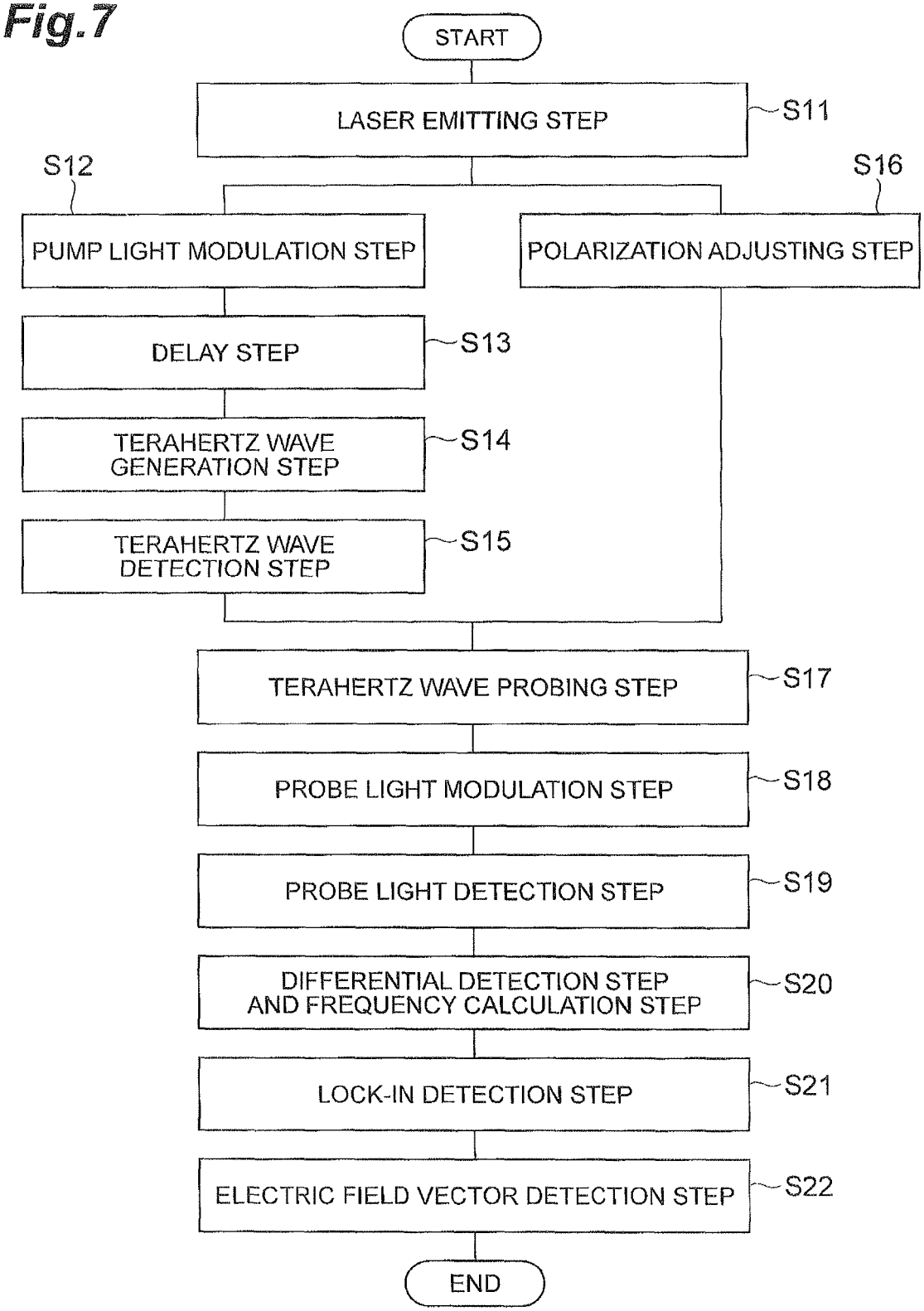

ELECTRIC FIELD VECTOR DETECTION METHOD AND ELECTRIC FIELD VECTOR DETECTION DEVICE

TECHNICAL FIELD

The present invention relates to an electric field vector detection method and an electric field vector detection device for detecting an electric field vector of a terahertz wave.

BACKGROUND

Methods for detecting an electric field vector of a terahertz wave include, roughly, (A) methods where components in two axial directions orthogonal to each other (e.g. X axis and Y axis) are detected separately and synthesized thereafter and (B) methods where an electric field vector is directly detected. As one of the methods of (A), for example in non-patent literature 1 (M. B. Byrne, M. U. Shaukat, J. E. Cunningham, E. H. Linfield, and A. G. Davies, "Simultaneous measurement of orthogonal components of polarization in a free-space propagating terahertz signal using electro-optic detection, "Appl. Phys. Lett. Vol. 98, p. 151104 (2011)), a terahertz wave is divided into polarized components in two orthogonal axial directions and these polarized components are detected by two detection systems. Thereafter, the obtained two detection results are synthesized to detect an electric field vector of the terahertz wave.

Also, in non-patent literature 2 (N. C. J. van der Valk, W. A. M. van der Marel, and P. C. M. Planken, "Terahertz polarization imaging," Opt. Lett. Vol. 30, p. 2802 (2005)), polarization of probe light is caused to be circular polarization and a (111) crystal is used where a (111) surface of an optical isotropic medium is cut out as an electro-optic crystal for detection of a terahertz wave. In this method, the probe light having probed the terahertz wave is divided and detected by two detection systems for separately measuring terahertz waves in two orthogonal axial directions. Thereafter, the obtained two detection results are synthesized to detect an electric field vector of the terahertz wave.

Meanwhile, as one of the methods of (B), for example in non-patent literature 3 (N. Yasumatsu and S. Watanabe, "Precise real-time polarization measurement of terahertz electromagnetic waves by a spinning electro-optic sensor," Rev. Sci. Instrum. Vol. 83, p. 023104 (2012)), an electric field vector of a terahertz wave is detected based on a shift in detection signals of probe light when an electro-optic crystal for detection of a terahertz wave is rotated. Furthermore, in non-patent literature 4 (N. Nemoto, T. Higuchi, N. Kanda, K. Konishi, and M. Kuwata-Gonokami, "Highly precise and accurate terahertz polarization measurements based on electro-optic sampling with polarization modulation of probe pulse," Opt. Express vol. 22, p. 17915 (2014)), a (111) crystal is used where a (111) surface of an optical isotropic medium is cut out as an electro-optic crystal for detection of a terahertz wave and a polarization direction of probe light is rotated while linear polarization is maintained. An electric field vector of the terahertz wave is detected from a shift in detection signals associated with a shift in the polarization direction of the probe light.

In non-patent literature 5 (N. Yasumatsu, A. Kasatani, K. Oguchi, and S. Watanabe, "High-speed terahertz time-domain polarimeter based on an electro-optic modulation technique," Appl. Phys. Express vol. 7, p. 092401 (2014)), a (111) crystal is used where a (111) surface of an optical isotropic medium is cut out as an electro-optic crystal for detection of a terahertz wave and polarization of probe light is caused to be circular polarization, thereby probing the terahertz wave. The probe light having probed the terahertz wave is modulated by an electrooptical modulator and then an electric field vector of the terahertz wave is detected based on a shift in the modulated signals.

SUMMARY

In the aforementioned methods of (A), there may be a problem that it is difficult to accurately divide polarized components in two orthogonal directions in a terahertz wave, or components in two axial directions orthogonal to each other in probe light having probed the terahertz wave. Furthermore, there may be another problem that an optical system becomes complex since two detection systems are required for each of the components.

On the other hand, in the methods of non-patent literatures 3 and 4 of the methods of (B), rotation of a polarization direction of an electro-optic crystal or probe light results in a variation in influence of residual birefringence of the electro-optic crystal and therefore a scheme of compensating distortion in a signal or a variation in detection efficiency is required. Also, in the method of non-patent literature 5, there may be a problem that a signal waveform has a complex shape since obtained modulated signals are the sum of two frequency components. Therefore, to derive two frequency components, Fourier transform or the like is required for the modulated signals and thus signal processing may disadvantageously be complex.

The present invention is made in order to solve the above problems with an object of providing an electric field vector detection method and electric field vector detection device capable of accurately detecting an electric field vector of a terahertz wave without complicating signal processing.

In order to solve the above problem, an electric field vector detection method according to one aspect of the invention includes an electric field vector detection method for detecting an electric field vector of a terahertz wave, where ultrashort pulsed light is used as probe light and an electro-optic crystal, where a (111) surface of an optical isotropic medium is cut out, is used as a terahertz wave detection element for detecting the terahertz wave. The method includes: causing polarization of the probe light to be circular polarization; allowing the probe light having circular polarization to enter the terahertz wave detection element and probing the terahertz wave; modulating the probe light, having probed the terahertz wave, by a rotating analyzer and detecting the modulated probe light by a photodetector; performing lock-in detection of a detection signal from the photodetector by a lock-in detector using a frequency based on a rotational frequency of the rotating analyzer as a reference signal; and detecting an electric field vector of the terahertz wave based on a detection signal from the lock-in detector.

In this electric field vector detection method, an electro-optic crystal, where a (111) surface of an optical isotropic medium is cut out, is used as a terahertz wave detection element and probe light of ultrashort pulsed light is caused to have circular polarization, thereby probing a terahertz wave. This allows for uniquely determining an electric field vector of a terahertz wave from polarization of the probe light after probing, thereby allowing for directly detecting the electric field vector of the terahertz wave. Also, the probe light is modulated into a sine wave shape by a rotating analyzer and thus complex signal processing of the modulated signal is not required. Therefore, an electric field vector of the terahertz wave can be accurately detected based on a detection signal from the lock-in detector having a high noise removing capability. Furthermore, since polarization of the probe light incident on the terahertz wave detection element does not change, a problem in non-patent literatures 3 and 4 that a detection signal varies due to an influence by unevenness of the electro-optic crystal can be avoided.

Moreover, amplitude of an electric field vector of the terahertz wave may be detected based on amplitude of the detection signal from the lock-in detector and a direction of an electric field vector of the terahertz wave may be detected based on a phase of the detection signal from the lock-in detector. This allows for uniquely determining an electric field vector of the terahertz wave based on the detection result from the lock-in detector.

Incidentally, as the lock-in detector, a dual phase lock-in detector may be used. Using the dual phase lock-in detector allows for detecting components in two axial directions, orthogonal to each other, of an electric field vector at a time.

Also, in the method, a terahertz wave generating element for generating a terahertz wave by incidence of pump light may be used. The method may further include: branching the ultrashort pulsed light into the probe light and the pump light; and modulating, in a cyclic manner, the pump light incident on the terahertz wave generating element by an optical modulator. This allows for removing a frequency component other than a modulation frequency of the terahertz wave, thereby allowing for making a measurement with low noise.

Moreover, when a rotational frequency of the rotating analyzer is defined as $f_1$ and a modulation frequency of the pump light is defined as $f_2$, lock-in detection may be performed while a frequency of a reference signal in the lock-in detector is defined as $f_2 \pm 2f_1$. This allows for substantially increasing a frequency in lock-in detection, thereby mitigating 1/f noise.

Furthermore, an electric field vector detection device according to one aspect of the invention includes an electric field vector detection device for detecting an electric field vector of a terahertz wave. The device includes: a polarization adjusting unit configured to cause polarization of probe light of ultrashort pulsed light to be circular polarization; a terahertz wave detection element including an electro-optic crystal, where a (111) surface of an optical isotropic medium is cut out; a rotating analyzer configured to modulate the probe light having probed the terahertz wave; a photodetector configured to detect the probe light having been modulated by the rotating analyzer; a lock-in detector configured to perform lock-in detection of a detection signal from the photodetector using a frequency based on a rotational frequency of the rotating analyzer as a reference signal; and an electric field vector detection unit configured to detect an electric field vector of the terahertz wave based on a detection signal from the lock-in detector.

In this electric field vector detection device, an electro-optic crystal, where a (111) surface of an optical isotropic medium is cut out, is used as the terahertz wave detection element and probe light of ultrashort pulsed light is caused to have circular polarization, thereby probing a terahertz wave. This allows for uniquely determining an electric field vector of the terahertz wave from polarization of the probe light after probing, thereby allowing for directly detecting an electric field vector of the terahertz wave. Also, the probe light is modulated into a sine wave shape by a rotating analyzer and thus complex signal processing of the modulated signal is not required. Therefore, an electric field vector of the terahertz wave can be accurately detected based on a detection signal from the lock-in detector having a high noise removing capability. Furthermore, since polarization of the probe light incident on the terahertz wave detection element does not change, a problem in non-patent literatures 3 and 4 that a detection signal varies due to an influence by unevenness of the electro-optic crystal can be avoided.

Moreover, the electric field vector detection unit may detect amplitude of an electric field vector of the terahertz wave based on amplitude of the detection signal from the lock-in detector and a direction of an electric field vector of the terahertz wave based on a phase of the detection signal from the lock-in detector. This allows for uniquely determining an electric field vector of the terahertz wave based on the detection result from the lock-in detector.

Incidentally, the lock-in detector may be a dual phase lock-in detector. Using the dual phase lock-in detector allows for detecting components in two axial directions, orthogonal to each other, of an electric field vector at a time.

Also, the device may further include: a terahertz wave generating element configured to generate the terahertz wave by incidence of pump light; a branching unit configured to branch the ultrashort pulsed light into the probe light and the pump light; and an optical modulator configured to modulate the pump light in a cyclic manner. This allows for removing a frequency component other than a modulation frequency of the terahertz wave, thereby allowing for making a measurement with low noise.

Moreover, when a rotational frequency of the rotating analyzer is defined as $f_1$ and a modulation frequency of the pump light is defined as $f_2$, the lock-in detector may perform lock-in detection while defining a frequency of the reference signal as $f_2 \pm 2f_1$. This allows for substantially increasing a frequency in lock-in detection, thereby mitigating 1/f noise.

As described above, according to one aspect of the invention, an electric field vector of a terahertz wave may be accurately detected without complicating signal processing.

BRIEF DESCRIPTION OF THE DRAWINGS

FIG. 7 is a flowchart illustrating an electric field vector detection method according to the second embodiment.

DETAILED DESCRIPTION

Hereinafter, preferable embodiments of an electric field vector detection method and an electric field vector detection device according to the present invention will be described in detail with reference to the drawings.

First Embodiment

Figure 1:
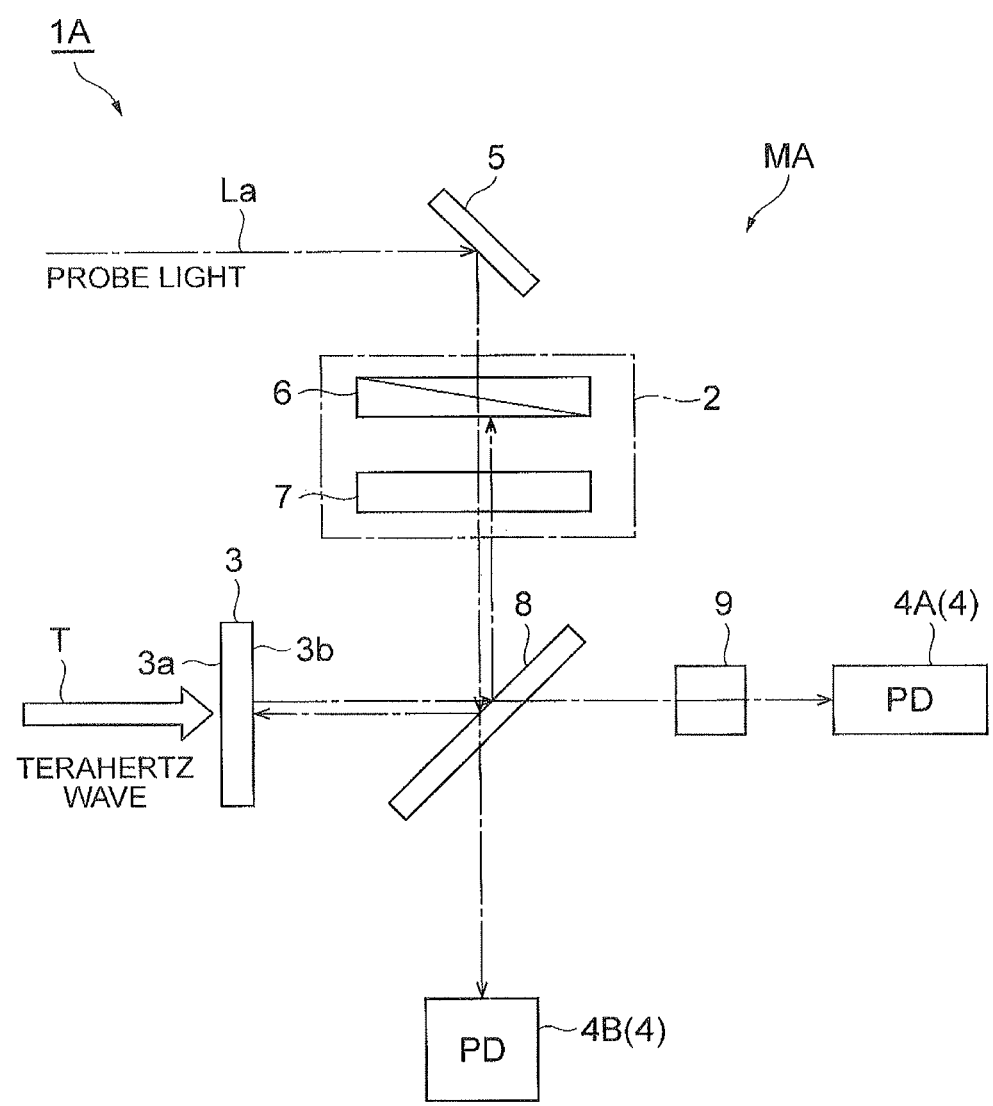
FIG. 1 is a diagram illustrating an optical system of an electric field vector detection device according to a first embodiment.

FIG. 1 is a diagram illustrating an optical system of an electric field vector detection device according to a first embodiment. As illustrated in FIG. 1, an optical system MA of an electric field vector detection device 1A includes a polarization adjusting unit 2 for adjusting polarization of probe light La, a terahertz wave detection element 3 for detecting a terahertz wave T, and a photodetector 4 (a first photodetector 4A and a second photodetector 4B) for detecting the probe light La.

The probe light La is emitted from, for example, a light source for emitting a femtosecond pulsed laser. The emitted light has, for example, a wavelength of 800 nm, a pulse width of 100 fs, and a repetition frequency of 100 MHz. The probe light La is guided to the polarization adjusting unit 2 via a mirror 5. The polarization adjusting unit 2 includes a polarizer 6 and a λ/4 wavelength plate 7. The probe light La guided to the polarization adjusting unit 2 is caused to have linear polarization in a predetermined direction by the polarizer 6 and then is caused to have circular polarization by the λ/4 wavelength plate 7.

The probe light La having circular polarization is divided into two by a non-polarizing beam splitter 8 while maintaining the polarization thereof. One of the divided probe light La is guided to the terahertz wave detection element 3 while the other is guided to the second photodetector 4B.

The terahertz wave detection element 3 includes, for example, an electro-optic crystal where a (111) surface of ZnTe of an optical isotropic medium is cut out. One surface 3a of the terahertz wave detection element 3 is an incident surface where the terahertz wave T enters. The surface 3a transmits the terahertz wave T and is coated with reflection coating for reflecting the probe light La. The opposite surface 3b of the terahertz wave detection element 3 is an incident surface where the probe light La enters. The opposite surface 3b is coated with antireflection coating for suppressing reflection of the probe light La.

Figure 2:
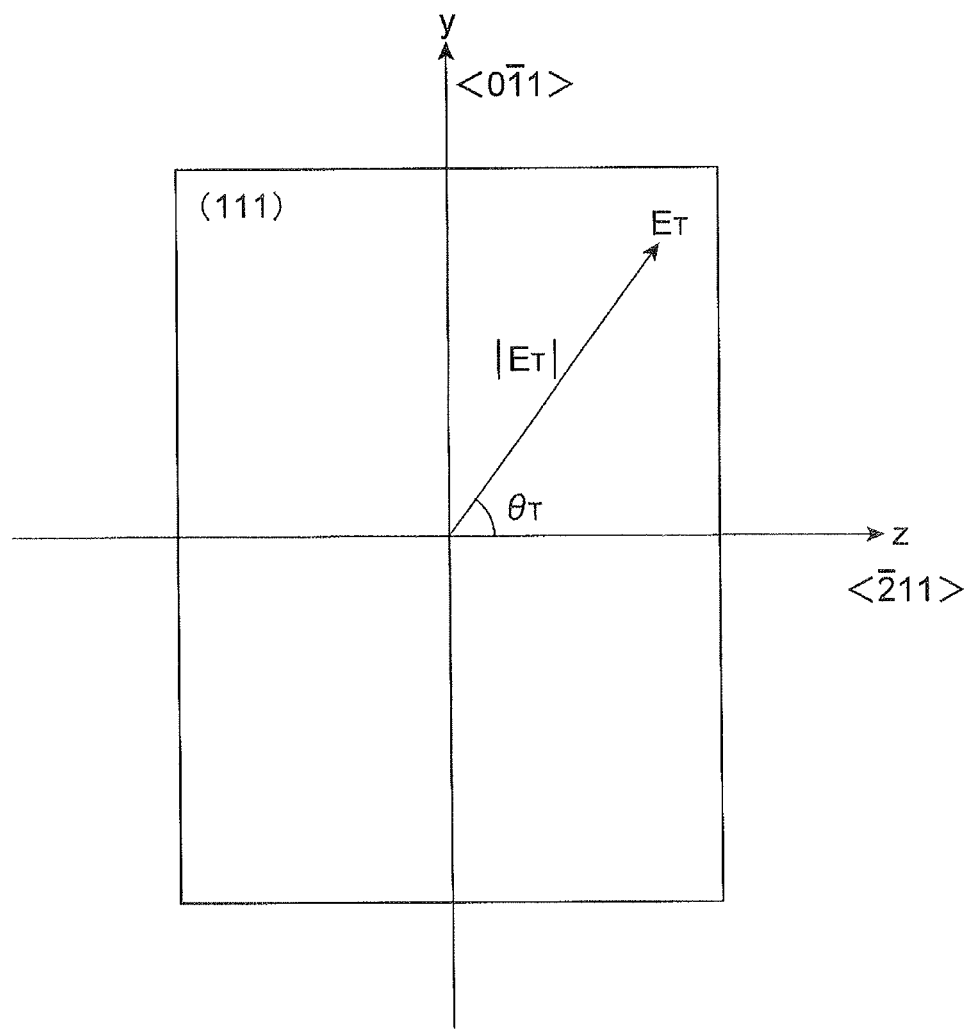
FIG. 2 is a diagram illustrating an electric field vector of a terahertz wave in a terahertz wave detection element.

FIG. 2 is a diagram illustrating an electric field vector of a terahertz wave in a terahertz wave detection element. As illustrated in FIG. 2, electric field vector $E_T$ of the terahertz wave T is represented by amplitude $|E_T|$ and direction $\theta_T$. Direction $\theta_T$ is defined where a <-211> direction in the (111) surface of ZnTe is defined as $\theta°$, which is used as a reference for defining a <0-11> direction as the normal direction. When an inclination of an electric field of the terahertz wave T to the <-211> direction is $2\theta$, birefringence is induced toward $-\theta$. The magnitude of birefringence induced according to the magnitude of the terahertz wave T is constant in any direction.

The probe light La having entered the terahertz wave detection element 3 is modulated by an electric field, as of the entering timing, of the terahertz wave T and the polarization thereof is changed to elliptical polarization. The probe light La having probed the terahertz wave T is reflected by the surface 3a of the terahertz wave detection element 3 and enters the non-polarizing beam splitter 8. One of divided probe light La enters the rotating analyzer 9 and the other becomes return light.

The rotating analyzer 9 is an element having an analyzer rotating in a plane by a motor or the like. When the probe light La enters the analyzer, only certain linear polarization is output. Therefore, when the analyzer rotates, the probe light La is modulated. The probe light La having been modulated by the rotating analyzer 9 enters the first photodetector 4A. The return light is caused to have elliptical polarization close to linear polarization by the λ/4 wavelength plate 7 and the most part of the light is blocked by the polarizer 6.

The first photodetector 4A and the second photodetector 4B are, for example, photodiodes. The first photodetector 4A detects the probe light La having probed the terahertz wave T and having been modulated by the rotating analyzer 9. The second photodetector 4B is used for monitoring power variations and detects the probe light La transmitted by the non-polarizing beam splitter 8 without having been guided to the terahertz wave detection element 3.

Figure 3:
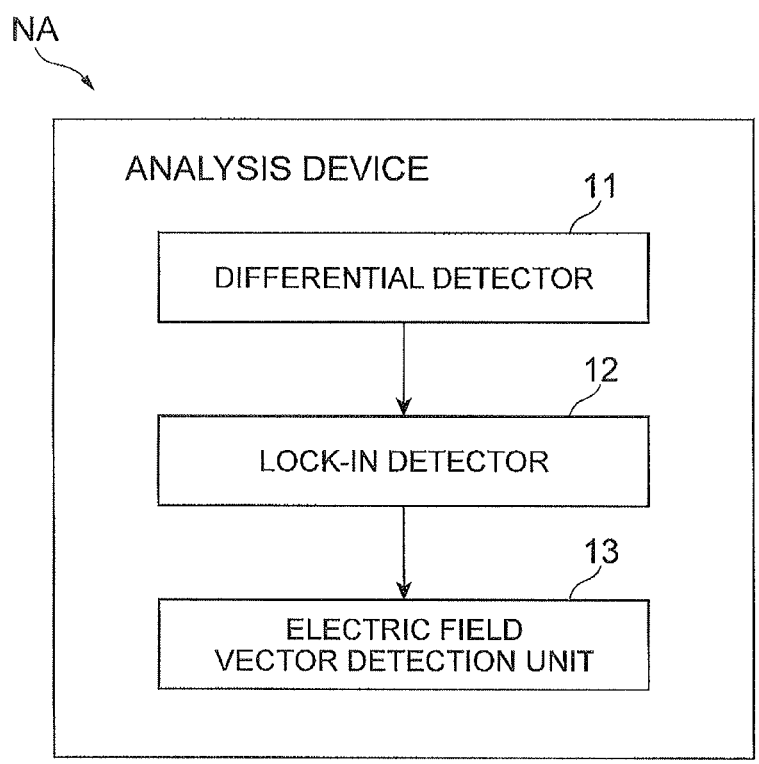
FIG. 3 is a block diagram illustrating an exemplary configuration of an analysis device connected to the optical system of the electric field vector detection device illustrated in FIG. 1.

FIG. 3 is a block diagram illustrating an exemplary configuration of an analysis device NA connected to the optical system MA of the electric field vector detection device 1A described above. As illustrated in FIG. 3, the analysis device NA includes a differential detector 11, a lock-in detector 12, and an electric field vector detection unit 13.

The differential detector 11 detects a difference between a detection signal from the first photodetector 4A and a detection signal from the second photodetector 413. The differential detector 11 outputs, to the lock-in detector 12, a detection signal based on a difference between the detection signal from the first photodetector 4A and the detection signal from the second photodetector 4B. Detecting the difference allows for removing a power variation component of the probe light La. Here, it is preferable that sensitivities of the first photodetector 4A and the second photodetector 4B are adjusted such that the intensity of the detection signal from the differential detector 11 equals zero when the terahertz wave T is not incident and the rotating analyzer 9 is not disposed.

The lock-in detector 12 performs lock-in detection of the detection signal from the first photodetector 4A (here, the detection signal from the differential detector 11). The lock-in detector 12 according to the embodiment is a dual phase lock-in detector which simultaneously detects amplitude and a phase of a detection signal which shifts in synchronization with a frequency of the reference signal. The detection signal from the differential detector 11 shifts by one cycle when the rotating analyzer 9 rotates by ½ revolution. Therefore, when a rotational frequency of the rotating analyzer 9 is defined as $f_1$, a frequency of the reference signal of the lock-in detector 12 can be defined as $2f_1$. The detection signal from the lock-in detector 12 is output to the electric field vector detection unit 13. Rotational frequency $f_1$ is, for example, 20 to 100 Hz.

The electric field vector detection unit 13 detects an electric field vector of the terahertz wave T based on the detection signal from the lock-in detector 12. The electric field vector detection unit 13 includes, physically, a computer system including a CPU, memory, communication interface, etc.

The following relationships hold for amplitude $A_L$ and phase $\phi_L$ of the detection signal from the lock-in detector 12 and amplitude $|E_T|$ and direction $\theta_T$ of an electric field vector of the terahertz wave T. In the formula below, $A_C$ denotes a constant determined based on the thickness and a nonlinear optical constant of the electro-optic crystal used as the terahertz wave detection element 3, a wavelength of the probe light La, or the like. The following formulas allow for uniquely determining an electric field vector of the terahertz wave T based on the detection result from the lock-in detector 12.

$$A_L = \frac{1}{2}\sin A_C |E_T| \qquad \text{[Formula 1]}$$

$$\phi_L = \frac{\pi}{2} - \theta_T \qquad \text{[Formula 2]}$$

Note that the following formula holds when amplitude of an electric field vector of the terahertz wave T is substantially small. In such a case, amplitude $A_L$ of the detection signal from the lock-in detector 12 may be used, as it is, as amplitude $|E_T|$ of an electric field vector of the terahertz wave T.

$$\sin A_C |E_T| \approx A_C |E_T| \qquad \text{[Formula 3]}$$

Also, the dual phase lock-in detector can separately output $A_L \cos \phi_L$ and $A_L \sin \phi_L$ according to a phase of the reference signal. When amplitude of an electric field vector of the terahertz wave T is substantially small, the following formulas hold for these outputs and components in the two axial directions orthogonal to each other in an electric field vector of the terahertz wave T. Therefore, values $E_{Tx}$ and $E_{Ty}$ proportional to the components in the two axial directions orthogonal to each other in an electric field vector of the terahertz wave T can be obtained based on the two outputs from the lock-in detector 12.

$$E_{Tx} \propto A_L \sin \phi_L \qquad \text{[Formula 4]}$$

$$E_{Ty} \propto A_L \cos \phi_L \qquad \text{[Formula 5]}$$

Figure 4:
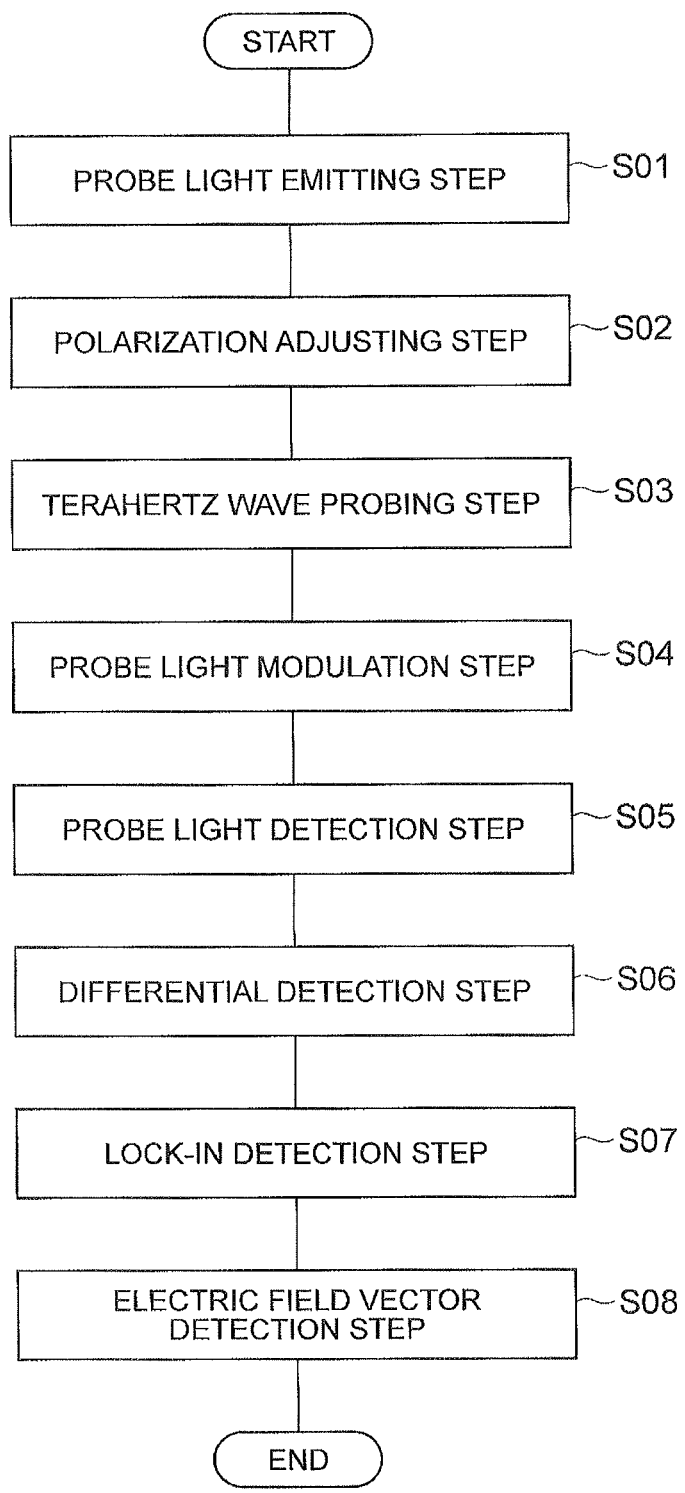
FIG. 4 is a flowchart illustrating an electric field vector detection method according to the first embodiment.

Next, an electric field vector detection method according to the first embodiment will be described. FIG. 4 is a flowchart illustrating the electric field vector detection method according to the first embodiment. This electric field vector detection method is performed using the aforementioned electric field vector detection device 1A.

As illustrated in FIG. 4, in this electric field vector detection method, the probe light La of ultrashort pulsed light is first emitted from a light source (not shown) (step S01: probe light emitting step). The probe light La is guided to the polarization adjusting unit 2, whereby polarization thereof is adjusted to circular polarization (step S02: polarization adjusting step).

The probe light La having circular polarization enters the terahertz wave detection element 3 and probes the terahertz wave T thereat (step S03: terahertz wave probing step). Here, polarization of the terahertz wave T is changed according to an electric field vector of the terahertz wave T. The probe light La after probing is modulated by the rotating analyzer 9 (step S04: probe light modulation step) and then detected by the first photodetector 4A (step S05: probe light detection step). Incidentally, the probe light La that was not used for probing is detected by the second photodetector 4B.

Next, detection signals from the first photodetector 4A and the second photodetector 4B are separately output to the differential detector 11, where differential detection is performed (step S06: differential detection step). Furthermore, a detection signal from the differential detector 11 is output to the lock-in detector 12, which performs lock-in detection using a frequency twice the rotational frequency of the rotating analyzer 9 as the reference signal (step S07: lock-in detection step). The detection signal from the lock-in detector 12 is then output to the electric field vector detection unit 13, where amplitude and a direction of an electric field vector of the terahertz wave T are detected based on amplitude and a phase of the detection signal from the lock-in detector 12 (step S08: electric field vector detection step).

As described above, in this electric field vector detection device 1A, an electro-optic crystal, where a (111) surface of an optical isotropic medium is cut out, is used as the terahertz wave detection element 3 and the probe light La of ultrashort pulsed light is caused to have circular polarization, thereby probing the terahertz wave T. This allows for uniquely determining an electric field vector of the terahertz wave T from polarization of the probe light La after probing, thereby allowing for directly detecting an electric field vector of the terahertz wave T.

Also, the probe light La is modulated into a sine wave shape by the rotating analyzer 9 and thus complex signal processing of the modulated signal is not required. Therefore, an electric field vector of the terahertz wave T can be accurately detected based on the detection signal from the lock-in detector 12 having a high noise removing capability. Furthermore, since polarization of the probe light La incident on the terahertz wave detection element 3 does not change, a problem that a detection signal varies due to an influence by unevenness of the electro-optic crystal can be avoided.

Moreover, the electric field vector detection unit 13 detects amplitude of an electric field vector of the terahertz wave T based on amplitude of the detection signal from the lock-in detector 12 and a direction of an electric field vector of the terahertz wave T based on a phase of the detection signal from the lock-in detector 12. This allows for uniquely determining an electric field vector of the terahertz wave T based on the detection result from the lock-in detector 12. Furthermore, using a dual phase lock-in detector as the lock-in detector 12 allows for detecting components in two axial directions, orthogonal to each other, of an electric field vector at a time.

Second Embodiment

Figure 5:
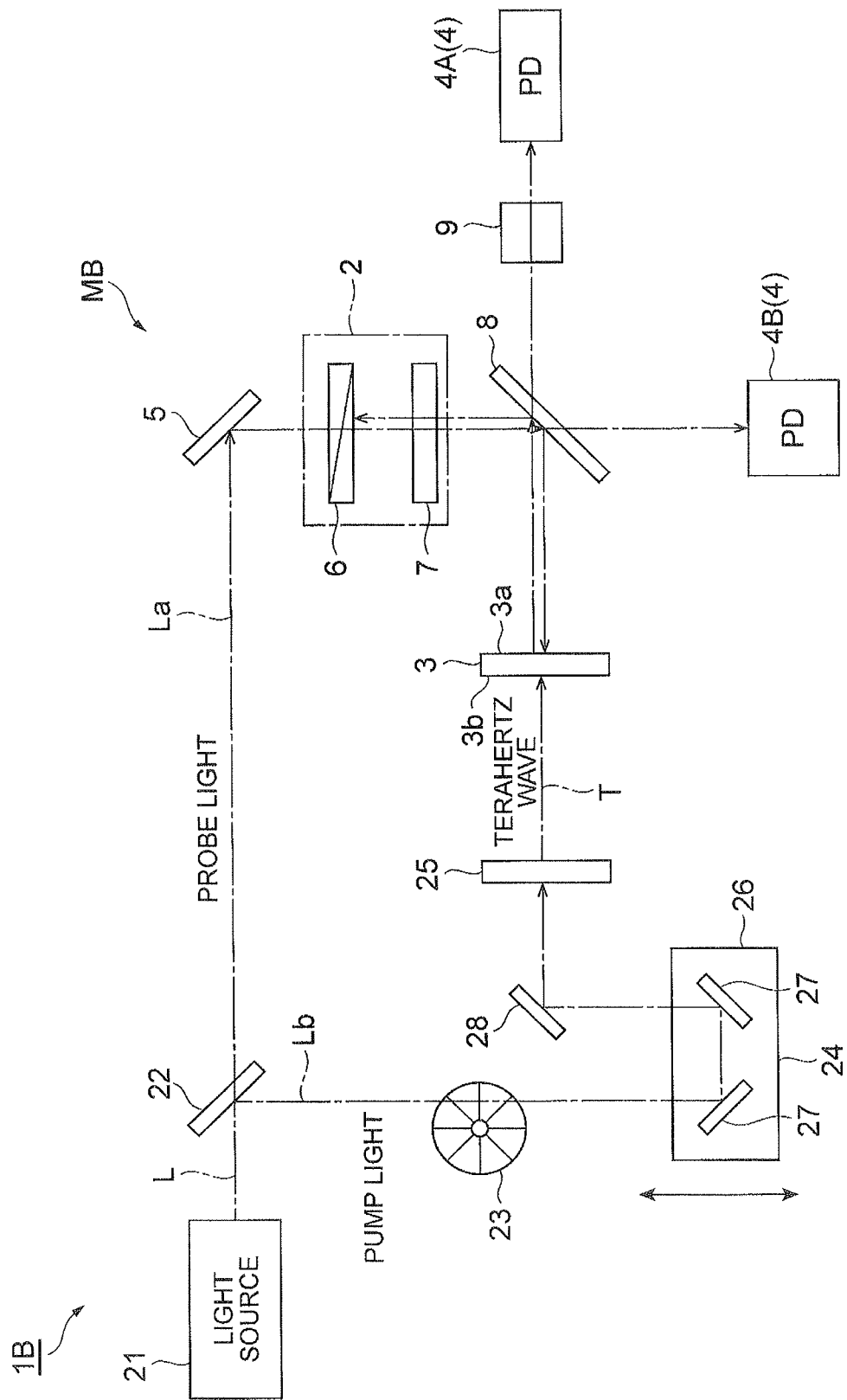
FIG. 5 is a diagram illustrating an optical system of an electric field vector detection device according to a second embodiment.

FIG. 5 is a diagram illustrating an optical system of an electric field vector detection device according to a second embodiment. As illustrated in FIG. 5, an optical system MB of an electric field vector detection device 1B according to the second embodiment differs from the electric field vector detection device 1A according to the first embodiment in that ultrashort pulsed light is branched into probe light La and pump light Lb.

More specifically, in the optical system MB of the electric field vector detection device 1B, in addition to the configuration of the first embodiment, a light source 21 for emitting a femtosecond pulsed laser, a beam splitter 22 for branching outgoing light L from the light source 21 into the probe light La and the pump light Lb, an optical modulator 23 for modulating the pump light Lb in a cyclic manner, a delay stage 24 for delaying the pump light Lb in relation to the probe light La, and a terahertz wave generating element 25 for generating a terahertz wave by incidence of the pump light Lb are disposed.

The femtosecond pulsed laser emitted from the light source 21 has, for example, a wavelength of 800 nm, a pulse width of 100 fs, a repetition frequency of 100 MHz, and an average output power of 500 mW. The optical modulator 23 is, for example, an optical chopper and modulates, in terms of time, the pump light Lb with a modulation frequency of $f_2$. Modulation frequency $f_2$ is, for example, 1 to 200 kHz. The delay stage 24 includes, for example, a stage 26 reciprocally movable in a light axial direction of the pump light Lb having been branched by the beam splitter 22 and a pair of mirrors 27, 27 for reflecting the pump light Lb. The pump light Lb that has passed the delay stage 24 is then guided to the terahertz wave generating element 25 by a mirror 28.

The terahertz wave generating element 25 includes, for example, a nonlinear optical crystal such as ZeTe, an antenna element such as an optical switch using GaAs, a semiconductor such as InAs, or a superconductor. A pulse of the terahertz wave T generated from such an element is generally a several picoseconds. When a nonlinear optical crystal is used as the terahertz wave generating element 25, the pump light Lb incident on the terahertz wave generating element 25 is converted to the terahertz wave T by a nonlinear optical effect. The generated terahertz wave T enters the terahertz wave detection element 3.

Figure 6:
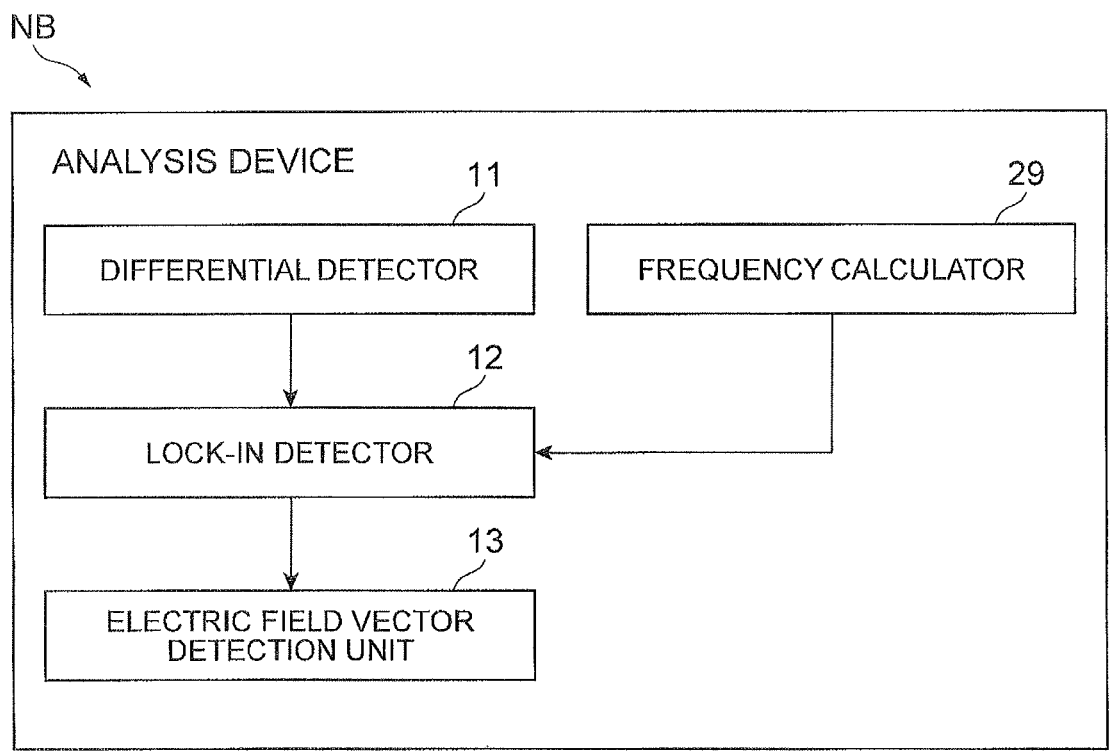
FIG. 6 is a block diagram illustrating an exemplary configuration of an analysis device connected to the optical system of the electric field vector detection device illustrated in FIG. 5.

FIG. 6 is a block diagram illustrating an exemplary configuration of an analysis device NB connected to the optical system MB of the electric field vector detection device 1B described above. As illustrated in FIG. 6, the analysis device NB is different from the analysis device NA of the first embodiment in that the analysis device NB further includes a frequency calculator 29.

The frequency calculator 29 generates a frequency based on the rotational frequency of the rotating analyzer 9 and a modulation frequency of the pump light Lb and outputs a reference signal to the lock-in detector 12. More specifically, when the rotational frequency of the rotating analyzer 9 is defined as $f_1$ and the modulation frequency of the pump light Lb is defined as $f_2$, the frequency calculator 29 generates a frequency of $f_2 \pm 2f_1$. The lock-in detector 12 performs lock-in detection of a detection signal output from the differential detector 11 with the reference signal of frequency $f_2 \pm 2f_1$.

FIG. 7 is a flowchart illustrating the electric field vector detection method according to the second embodiment. This electric field vector detection method is performed using the aforementioned electric field vector detection device 1B.

As illustrated in FIG. 7, in this electric field vector detection method, the outgoing light L of ultrashort pulsed light is first emitted from the light source 21 (step S11: laser emitting step). The outgoing light L emitted from the light source 21 is divided by a beam splitter 22 into the probe light La and the pump light Lb. The pump light Lb is time modulated by the optical modulator 23 (step S12: pump light modulation step) and delayed by passing the delay stage 24 (step S13: delay step).

The pump light Lb having passed the delay stage 24 enters the terahertz wave generating element 25 and generates the terahertz wave T thereat (step S14: terahertz wave generation step). The terahertz wave T generated by the terahertz wave generating element 25 then enters the terahertz wave detection element 3 (step S15: terahertz wave detection step).

Meanwhile, the probe light La is guided to the polarization adjusting unit 2, whereby polarization thereof is adjusted to circular polarization (step S16: polarization adjusting step). The probe light La having circular polarization enters the terahertz wave detection element 3 and probes the terahertz wave T thereat (step S17: terahertz wave probing step). Here, polarization of the terahertz wave T is changed according to an electric field vector of the terahertz wave T.

The probe light La after probing is modulated by the rotating analyzer 9 (step S18: probe light modulation step) and then detected by the first photodetector 4A (step S19: probe light detection step). Incidentally, the probe light La that was not used for probing is detected by the second photodetector 4B.

Next, detection signals from the first photodetector 4A and the second photodetector 4B are separately output to the differential detector 11, where differential detection is performed. Furthermore, the frequency calculator 29 generates a frequency based on the rotational frequency of the rotating analyzer 9 and the modulation frequency of the pump light Lb and outputs the frequency to the lock-in detector 12 (step S20: differential detection step and frequency calculation step).

When a detection signal from the differential detector 11 is output to the lock-in detector 12, lock-in detection is performed with the frequency having been generated by the frequency calculator 29 as a reference signal (step S21: lock-in detection step). A detection signal from the lock-in detector 12 is then output to the electric field vector detection unit 13, where amplitude and a direction of an electric field vector of the terahertz wave T are detected based on amplitude and a phase of the detection signal from the lock-in detector 12 (step S22: electric field vector detection step).

Also in the electric field vector detection device 1B, an electro-optic crystal, where a (111) surface of an optical isotropic medium is cut out, is used as the terahertz wave detection element 3 and the probe light La of ultrashort pulsed light is caused to have circular polarization, thereby probing the terahertz wave T. This allows for uniquely determining an electric field vector of the terahertz wave T from polarization of the probe light La after probing, thereby allowing for directly detecting an electric field vector of the terahertz wave T.

Also, the probe light La is modulated into a sine wave shape by the rotating analyzer 9 and thus complex signal processing of the modulated signal is not required. Therefore, an electric field vector of the terahertz wave T can be accurately detected based on the detection signal from the lock-in detector 12 having a high noise removing capability. Furthermore, since polarization of the probe light La incident on the terahertz wave detection element 3 does not change, a problem that a detection signal varies due to an influence by unevenness of the electro-optic crystal can be avoided.

Also, in this electric field vector detection device 1B, ultrashort pulsed light is branched into the probe light La and the pump light Lb and the pump light Lb is modulated in a cyclic manner by the optical modulator 23. The terahertz wave T incident on the terahertz wave detection element 3 is modulated in a cyclic manner. By sweeping the delay time of the pump light Lb by the delay stage 24, an incidence timing of the terahertz wave T on the terahertz wave detection element 3 is varied. This allows for serially detecting a shift in an electric field vector of the terahertz wave T over time, thereby allowing for detecting a time waveform of the terahertz wave T including polarization information.

Moreover, similar to the first embodiment, the electric field vector detection unit 13 detects amplitude of an electric field vector of the terahertz wave T based on amplitude of the detection signal from the lock-in detector 12 and a direction of an electric field vector of the terahertz wave T based on a phase of the detection signal from the lock-in detector 12. This allows for uniquely determining an electric field vector of the terahertz wave T based on the detection result from the lock-in detector 12.

Furthermore, using a dual phase lock-in detector as the lock-in detector 12 allows for detecting components in two axial directions, orthogonal to each other, of an electric field vector at a time. Moreover, in the electric field vector detection device 1B, when the rotational frequency of the rotating analyzer 9 is defined as $f_1$ and the modulation frequency of the pump light Lb is defined as $f_2$, lock-in detection is performed while the frequency of the reference signal in the lock-in detector 12 in defined as $f_2 \pm 2f_1$. This allows for substantially increasing a frequency in lock-in detection, thereby mitigating 1/f noise.

The present invention is not limited to the aforementioned embodiments. For example in the optical system MA, an isolator may be disposed such that the probe light La that has become return light does not reach the light source 21. Also, although the electro-optic crystal where the (111) surface of an optical isotropic medium of ZnTe is cut out has been shown as an example of the terahertz wave detection element 3, the electro-optic crystal may by a crystal where a (111) surface of another optical isotropic medium such as GaP is cut out.

Furthermore, in the embodiment above, the surface 3a of the terahertz wave detection element 3 reflects the probe light La; however, the terahertz wave detection element 3 may be configured to transmit the terahertz wave T and the probe light La coaxially therein. The first photodetector 4A may be a balance detector or a measurement system capable of detecting polarization. The first photodetector 4A and the second photodetector 4B may be AC connected to the differential detector 11 to remove DC components. The lock-in detection performed by the lock-in detector 12 may be either hardware lock-in or software lock-in.

Incidentally, the lock-in detector 12 may be a single phase lock-in detector. When using the single phase lock-in detector, an electric field vector of the terahertz wave T in one axial direction can be detected based on a detection signal therefrom. Therefore, when the lock-in detector is provided with a function for automatically setting a phase where a detection signal has the maximum amplitude, using this function allows for detecting a direction of an electric field vector of the terahertz wave T. This allows for detecting amplitude of an electric field vector of the terahertz wave T based on the amplitude of the detection signal from the lock-in detection.

What is claimed is:

1. An electric field vector detection method for detecting an electric field vector of a terahertz wave,
   wherein ultrashort pulsed light is used as probe light and an electro-optic crystal, where a (111) surface of an optical isotropic medium is cut out, is used as a terahertz wave detection element for detecting the terahertz wave, the method comprising:
   causing polarization of the probe light to be circular polarization;
   allowing the probe light having circular polarization to enter the terahertz wave detection element and probing the terahertz wave;
   modulating the probe light, having probed the terahertz wave, by a rotating analyzer and detecting the modulated probe light by a photodetector;
   performing lock-in detection of a detection signal from the photodetector by a lock-in detector using a frequency based on a rotational frequency of the rotating analyzer as a reference signal; and
   detecting an electric field vector of the terahertz wave based on a detection signal from the lock-in detector.

2. The electric field vector detection method according to claim 1,
   wherein amplitude of an electric field vector of the terahertz wave is detected based on amplitude of the detection signal from the lock-in detector, and, a direction of an electric field vector of the terahertz wave is detected based on a phase of the detection signal from the lock-in detector.

3. The electric field vector detection method according to claim 1,
   wherein a dual phase lock-in detector is used as the lock-in detector.

4. The electric field vector detection method according to claim 1,
   wherein a terahertz wave generating element configured to generate the terahertz wave by incidence of pump light is used,
   the method further comprising:
   branching the ultrashort pulsed light into the probe light and the pump light; and
   modulating, in a cyclic manner, the pump light incident on the terahertz wave generating element by an optical modulator.

5. The electric field vector detection method according to claim 4,
   wherein, when a rotational frequency of the rotating analyzer is defined as $f_1$ and a modulation frequency of the pump light is defined as $f_2$, lock-in detection is performed while a frequency of the reference signal in the lock-in detector is defined as $f_2 \pm 2f_1$.

6. An electric field vector detection device for detecting an electric field vector of a terahertz wave, the device comprising:
   a polarization adjusting unit configured to cause polarization of probe light of ultrashort pulsed light to be circular polarization;
   a terahertz wave detection element including an electro-optic crystal, where a (111) surface of an optical isotropic medium is cut out;
   a rotating analyzer configured to modulate the probe light having probed the terahertz wave;
   a photodetector configured to detect the probe light having been modulated by the rotating analyzer;
   a lock-in detector configured to perform lock-in detection of a detection signal from the photodetector using a frequency based on a rotational frequency of the rotating analyzer as a reference signal; and
   an electric field vector detection unit configured to detect an electric field vector of the terahertz wave based on a detection signal from the lock-in detector.

7. The electric field vector detection device according to claim 6,
   wherein the electric field vector detection unit detects amplitude of an electric field, vector of the terahertz wave based on amplitude of the detection signal from the lock-in detector and a direction of an electric field vector of the terahertz wave based on a phase of the detection signal from the lock-in detector.

8. The electric field vector detection device according to claim 6,
   wherein the lock-in detector is a dual phase lock-in detector.

9. The electric field vector detection device according to claims 6, further comprising:
   a terahertz wave generating element configured to generate the terahertz wave by incidence of pump light;

a branching unit configured to branch the ultrashort pulsed light into the probe light and the pump light; and an optical modulator configured to modulate the pump light in a cyclic manner.

10. The electric field vector detection device according to claim 9, wherein, when a rotational frequency of the rotating analyzer is defined as $f_1$ and a modulation frequency of the pump light is defined as $f_2$, the lock-in detector performs lock-in detection while defining a frequency of the reference signal as $f_2 \pm 2f_1$.

* * * * *